(12) United States Patent
Lee et al.

(10) Patent No.: US 8,354,222 B2
(45) Date of Patent: Jan. 15, 2013

(54) METHOD FOR DETECTING CANCER AND REAGENTS FOR USE THEREIN

(75) Inventors: Yao-Chang Lee, Hsinchu (TW); Pei-Yu Huang, Jinhu Town (TW); Ching-Iue Chen, Yuanlin Town (TW)

(73) Assignee: National Synchrotron Radiation Research Center, Hsinchu (TW)

( * ) Notice: Subject to any disclaimer, the term of this patent is extended or adjusted under 35 U.S.C. 154(b) by 622 days.

(21) Appl. No.: 12/459,537

(22) Filed: Jul. 2, 2009

(65) Prior Publication Data

US 2010/0216179 A1  Aug. 26, 2010

(30) Foreign Application Priority Data

Feb. 20, 2009 (TW) ................................ 98105394 A

(51) Int. Cl.
*C12Q 1/00* (2006.01)
(52) U.S. Cl. ............................. 435/4; 435/7.21; 356/301
(58) Field of Classification Search .................... None
See application file for complete search history.

(56) References Cited

U.S. PATENT DOCUMENTS 5,726,061 A  3/1998  Robbins et al.
6,187,591 B1  2/2001  Krepinsky et al.

OTHER PUBLICATIONS

Faolain E.O. et al., The potential of vibrational spectroscopy in the early detection of cervical cancer: an exciting emerging field; Proceedings of OptoIreland 2005, H.J. Byrne, E. Lewis, B. D. MacCraith, E. McGlynn, J.A. McLaughlin, G.D. O'Sullivan, A.G. Ryder, J.E. Walsh eds., SPIE (Jan. 1, 2005), vol. 5826, 25.*

Rehman S. et al., Raman spectroscopic analysis of breast cancer tissues: identifying differences between normal, invasive ductal carcinoma and ductal carcinoma in situ of the breast tissue, Journal of Raman Spectroscopy, 2007; 38: 1345-1351.*
Schomacker K.T. et al., Ultraviolet Laser-Induced Fluorescence of Colonic Tissue: Basic Biology and Diagnostic Potential, Lasers in Surgery and Medicine, 1992, vol. 12, pp. 63-78.*
Bogomolny E. et al., (Mar.-Apr. 2007)—Early spectral changes of cellular malignant transformation using Fourier transform infrared microspectroscopy, Journal of Biomedical Optics, Mar./Apr. 2007, vol. 12, No. 2, pp. 024003-024009.*
U2: Huang et al., (2008-2009)—A Kinetic Study of Capability of Wax Physisorption for Colorectal Cancer Diagnosis by Infrared Microspectroscopy, 14A1 BM—IR Microscopy, II—138; Published on the web at: http://www.nsrrc.org.tw/NsrrcWebSystem/UPLOADS%5CCHINESE%5CPUBLISH_YEARLY%5C2008~2009/appen2-pdf/appen2-166.pdf.*
V2: Cheng et al., (2009-2010)—An Innovative Kinetic Study of Oral Cavity Cancer Detection Using Synchrotron-based Infrared Microspectroscopy, 14A1 BM—IR Microscopy, II—166; Published on the web at: http://www.nsrrc.org.tw/NsrrcWebSystem/UPLOADS%5CCHINESE%5CPUBLISH_YEARLY%5C2009~2010/appen2-pdf/appen2-138.pdf.*

* cited by examiner

*Primary Examiner* — Jon P Weber
*Assistant Examiner* — Satyendra Singh
(74) *Attorney, Agent, or Firm* — Ming Chow; Sinorica, LLC

(57) ABSTRACT

A method for detecting cancer uses a first detection reagent containing a first adsorbent, which is physically adsorbed by biomedical sample. The first adsorbent comprises a long-chain ester wax containing 16-46 carbon atoms or a long-chain alkane wax containing 21-30 carbon atoms and a concentration of the first adsorbent is between 5% to 10% w/w. The present invention could be widely applied for detecting various cancers based on the differential physisorption of adsorbent. The present invention can provide a method for rapidly and non-invasively detecting cancers.

18 Claims, 12 Drawing Sheets
(10 of 12 Drawing Sheet(s) Filed in Color)

METHOD FOR DETECTING CANCER AND REAGENTS FOR USE THEREIN

FIELD OF THE INVENTION

The present invention relates to a method for detecting cancer, and more particularly to a method for detecting cancer based on physisorption kinetics of reagent.

DESCRIPTION OF THE PRIOR ART

At an early phase of cancer, it is difficult to diagnose cancer in a clinic as it is usually asymptomatic. Generally speaking, there is apparently symptomatic for a patient with cancer in the intermediate or advanced phase, which may seek medical assistance for diagnosing and cancer therapy, but by then cancer cells would have metastasized to other organs. Therefore, it is quite important for researcher to develop an easy and rapid method for detecting cancers of early phase.

Many tumor biomarkers, e.g. CEA (carcinoembryonic antigen) and EGTM (European Group on Tumour Marker), have been developed for various cancers in the past. However, poor issues of sensitivity and specificity for these biomarkers and time-consuming procedures have made these techniques unattractive. Therefore, the tumor markers are presently being applied for tracing relapse of cancers after cancer therapy rather than for the purpose of early diagnosis.

U.S. Pat. No. 5,726,061 discloses applications of biochemical enzymes for detecting disaccharide markers (-D-Gal(1-3)-D-GalNAc(1-Thr/Ser) and monosaccharide markers (2-acetamido-2-deoxy-D-galactose). However, specific antibodies production is a requisite for detecting various tumors antigen and therefore, the said method is limited.

U.S. Pat. No. 6,187,591 discloses using a Schiff's reagent to react with the colon mucosa for detecting the presence of the biomarker, a C12-C20 aliphatic aldehyde, of the colorectal cancer tissue, for early diagnosis for colorectal cancer. However, this diagnostic method is difficulty applied to cell level of detection.

In addition, genetic testing may be performed for detecting oral cavity cancer; however, this technique is complicated and time-consuming.

Therefore, it is highly desirable to develop a simple and rapid diagnostic technique for diagnosing various cancers at early phase.

SUMMARY OF THE INVENTION

The present invention is directed to provide a method for diagnosing cancer at early phase so that the cancer may be timely detected and treated.

The present invention is directed to a method based on physisorption kinetics of reagent for rapidly and non-invasively detecting cancers at early phase.

The present invention is also directed to reagents applied in the method for diagnosing cancers. According to an embodiment, the physisorption kinetics of the reagent for cancer tissue is dramatically different compared to that of the normal tissue, and therefore it is easily, rapidly and widely applied to detect various kinds of cancers.

In one embodiment, a method for detecting cancer includes providing a biomedical sample, performing a first adsorption step, performing a first desorption step and performing a first discrimination step. In the first adsorption step, the biomedical sample is immersed into a first detection reagent including a first adsorbent, which physically adsorbs onto the biomedical sample. A concentration of the first adsorbent is between 5% to 10% w/w and the first adsorbent comprises a long-chain ester wax containing 16-46 carbon atoms or a long-chain alkane wax containing 21-30 carbon atoms. In the first desorption step, the biomedical sample is immersed into a first desorption reagent and allowed to react for a first period of time. In the first discrimination step, the amount of residual of first adsorbent adsorbing on the biomedical sample is detected in comparison to an amount of residual of first adsorbent adsorbed onto a normal biomedical sample or a cancer biomedical sample to determine the distribution of cancer cells within the biomedical sample.

The objective, technologies, features and advantages of the present invention will become concrete from the following description in conjunction with the accompanying drawings wherein are proposed, by way of illustration and taking example, certain embodiments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above aspects and advantages of this invention will become to be more readily appreciated, that is, becomes easily to be understood by referring to the following detailed description aided with the accompanying drawings, wherein.

DESCRIPTION OF THE PREFERRED EMBODIMENT

The composition of membrane of a cancer cell is different from that of a normal cell, and thus physisorption capability of the cancer cell is different from that of a normal cell. The present invention employs the physisorption capability for differentiating a cancer cell from a normal cell.

Figure 1:
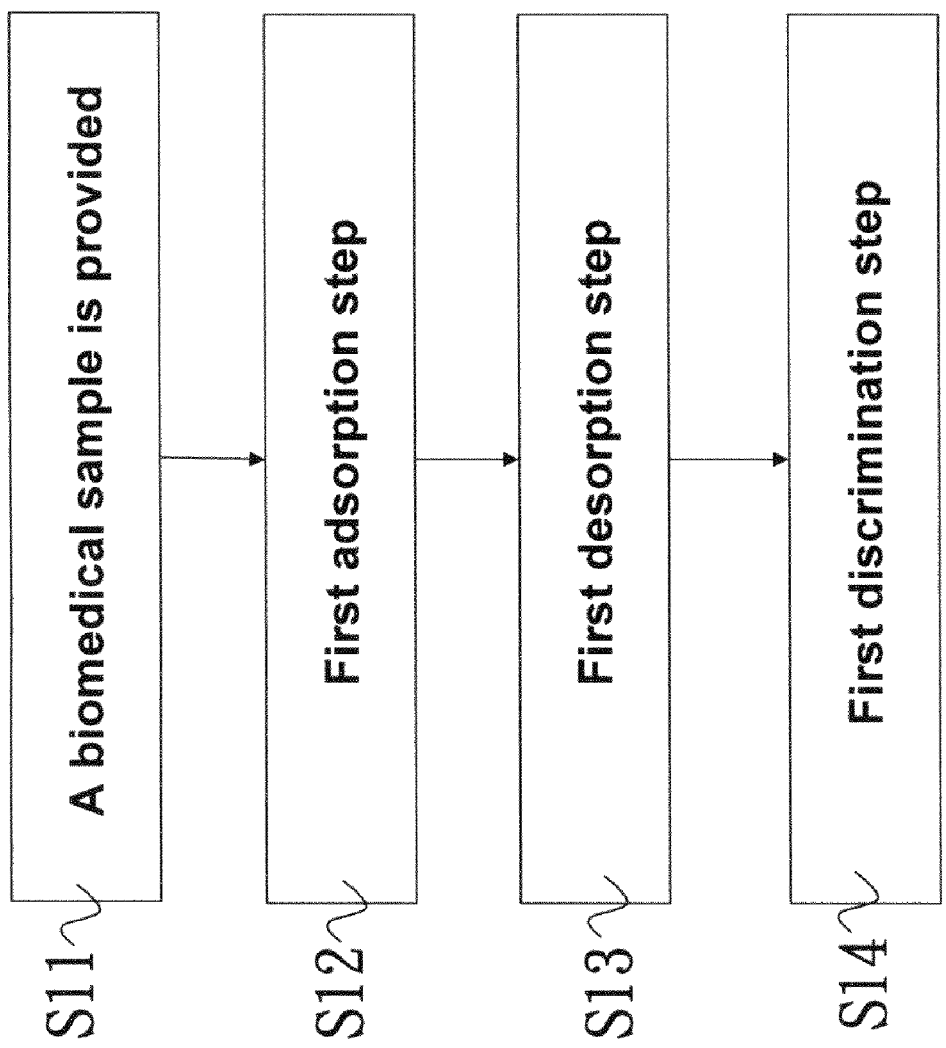
FIG. 1 is a flow chart illustrating a method for detecting cancer according to an embodiment of the present invention.

The present invention provides a method for detecting cancer based on above principle. Referring to FIG. 1, a flow chart illustrates a method for detecting cancer, which may be described as follows. At step S11, a biomedical sample including, such as a tissue section or cell lines, is provided.

At first reagent adsorption step S12, the biomedical sample is immersed into a first detection reagent comprising a first adsorbent, which is physically adsorbed onto the biomedical sample. The physisorption of the first adsorbent is greater for the cancer cells than that of the normal cells in the biomedical sample. For example, the first adsorbent comprises a long-chain ester wax containing 16-46 carbon atoms.

Alternatively, the physisorption capability of the first adsorbent is greater for the normal cells than that of the cancer cells in the biomedical sample. For example, the first adsorbent comprises a long-chain alkane wax containing 21-30 carbon atoms.

Next, at first reagent-desorption step S13, the biomedical sample is immersed into a first desorption reagent for a predetermined period of time. For example, the first desorption reagent comprises an organic solvent for desorbing the first adsorbent adsorbed onto the biomedical sample. The cells with comparatively less physisorption capability for the first adsorbent is much easier to be desorbed with the first desorption reagent, and vice versus.

The length of the predetermined time depends on several factors, such as the option and concentration of the first adsorbent and the first desorbing reagent. Additionally, according to differential physisorption capability of cancer cells at different stages of cancer. Accordingly, the predetermined time can be adjusted according to the amount of residual of adsorbed first adsorbent, which is the signpost for staging cancer. Therefore, based on the relative amount of residual of adsorbent, the cancer stages of the cancer samples may be rapidly determined.

At discrimination step S14, the amount of residual of the first adsorbent adhering onto the biomedical sample is determined for the distribution of cancer cells within the biomedical sample. In one embodiment, the amount residual of the first adsorbent adhering onto the biomedical sample is determined by the absorbance or intensity based on the integration in the spectral range of 3000-2800 $cm^{-1}$ for infrared spectrum or Raman scattering spectrum.

In another embodiment, the first detection reagent is homogeneously mixed with a specific fluorescent dye that is soluble in organic solvent and does not bind to lipid molecules, cell membrane or tissue samples. Preferably, the fluorescent dye comprises LC6500, 4-dicyanomethylene-2-methyl-6-p-dimethylamino styryl-4H-pyran (DCM), Allophycocyanin (APC) or APC-Cy7, for example. The amount of residual of the first adsorbent adsorbed onto the biomedical sample can be determined by measuring the intensity of the fluorescence.

The first reagent-desorption step S13 and the first discrimination step S14 may be repeated several times and compared to achieve an optimal condition for detection. As described above, the amount of residual of the first adsorbent onto the biomedical sample correlates to the length of time, a biomedical sample being immersed into the first desorbing reagent. The length of time for immersion may be adjusted by repeating the first desorption step S13 and the first discrimination step S14 several times to determine cancer stage at different regions of biomedical sample.

In one embodiment, a first pre-cleaning step may be performed prior to the first adsorption step S12, during which the biomedical sample is immersed into the first desorption reagent for a longer period of time than the predetermined period of time for removing impurities from the surface of the biomedical sample.

Figure 2:
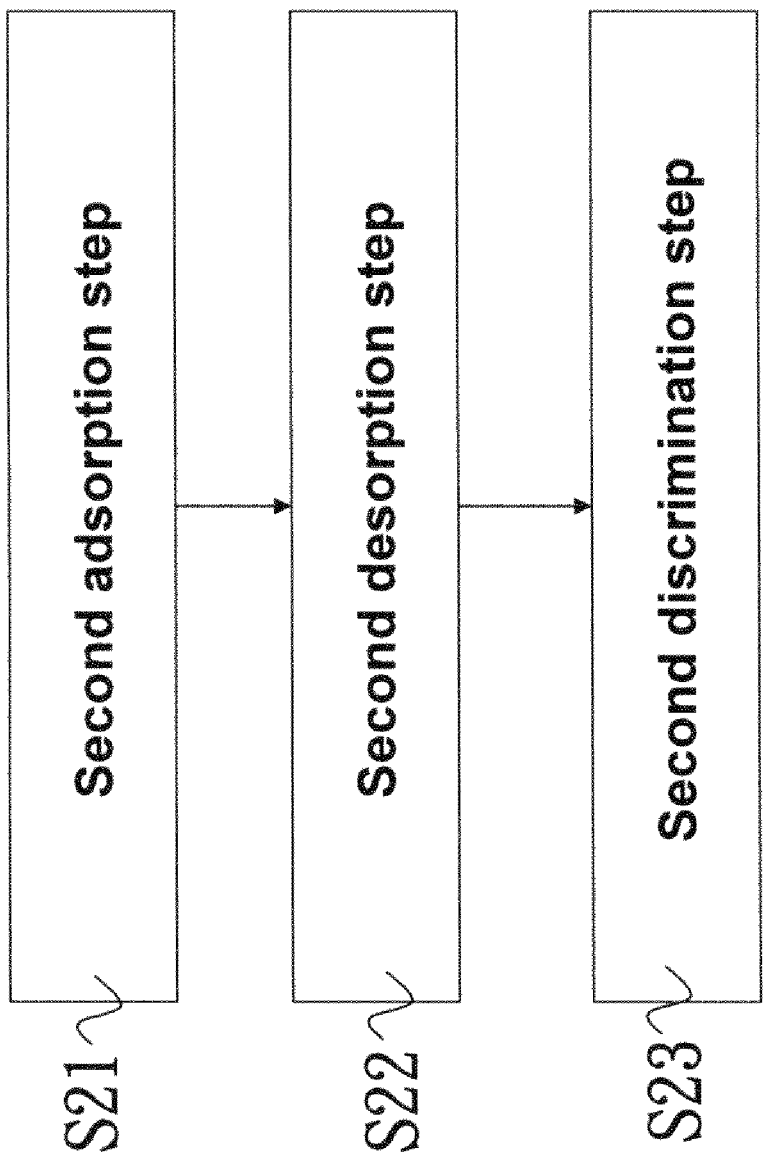
FIG. 2 is a flow chart illustrating a method for detecting cancer according to an embodiment of the present invention.

Referring to FIG. 2, a method for detecting cancer according to another preferred embodiment of the present invention is provided. The method, in addition to the steps illustrated in FIG. 1, further comprises the following steps. A second reagent-adsorption step S21 is performed during which the biomedical sample is immersed into a second detection reagent comprising a second adsorbent that would be adsorbed physically onto the biomedical sample. Next, a second desorption step S22 is performed, which includes immersing the biomedical sample into a second desorption reagent for a second period of time. The second desorption reagent comprises an organic solvent for desorbing the second adsorbent adhering onto the biomedical sample. Next, a second discrimination step S23 is performed, which includes measuring the amount of residual of the second adsorbent adhering onto the biomedical sample for identifying the distribution of cancer cells within the biomedical sample. The second reagent-desorbing step S22 and the second discrimination step S23 may be repeated several times, and the results are compared with each other to optimize the detection procedures.

As described above, the physisorption capability of the first adsorbent may be greater or less for cancer cells than that of normal cells within the biomedical sample. Therefore, in one preferred embodiment, two kinds of adsorbents are with greater and less physisorption capability to the cancer cells and the normal cells within the biomedical sample, respectively, and the residual for each adsorbent adhering onto biomedical sample is compared to identify the cancer cells distribution within the biomedical sample.

Further to the above description, the physisorption capability of the first adsorbent and the second adsorbent for the cancer cells may be greater and less than that of the normal cells within the biomedical sample, respectively. For example, the first adsorbent comprises a long-chain ester containing 16-46 carbon atoms; and the second adsorbent comprises a long-chain alkane containing 21-30 carbon atoms.

Alternatively, the physisorption capability of the first adsorbent for the cancer cells may be less and the second adsorbent may be greater than that of the normal cells within the biomedical sample, respectively. For example, the first adsorbent comprises a long-chain alkane containing 21-30 carbon atoms, and the second adsorbent comprises a long-chain ester containing 16-46 carbon atoms.

In one embodiment, the method for cancer detection comprises a second pre-cleaning step prior to the second adsorption step S21, which includes immersing the biomedical sample into the second desorption reagent for a longer time than the second predetermined time for removing impurities from the surface of biomedical sample.

The present invention may be described in detail by the following embodiments, which are presented for the purposes of illustrations and descriptions, and they are not intended to limit the scope of the present invention.

Embodiment 1

Colon Cancer Detection

This embodiment describes a method for determining colon cancer.

1. First, a sample of cell lines is fixed on a slide and then immersed into Dimethylbenzene (Xylene, $C_8H_{10}$) for 20 minutes. Next, the infrared spectrum and spectral image of the sample is acquired as the background as follows for determining cancer. An organic solvent, for example but not limited to, xylene and a detection reagent at 25 are employed, and the sample is dried at room temperature.

2. Next, the sample is immersed for 2 minutes into a xylene solution, $C_{25}H_{52}$ containing 5% w/w paraffin which serves as the first adsorbent, and then the sample dried at room temperature.

3. Next, the waxed sample of cell lines is immersed in xylene for 5 seconds to partially desorb the paraffin and then dried at room temperature. Next, the absorption spectra and spectral images of the waxed sample of cell lines fixed on a slide are taken. The infrared images of sample of cell lines adsorbing wax are obtained by measuring the absorbance of wax in the range of 3000-2800 $cm^{-1}$.

4. The above step 3 is repeated thrice, by immersing the sample for 5, 10 and 15 seconds in xylene for completely desorbing paraffin.

Figure 3:
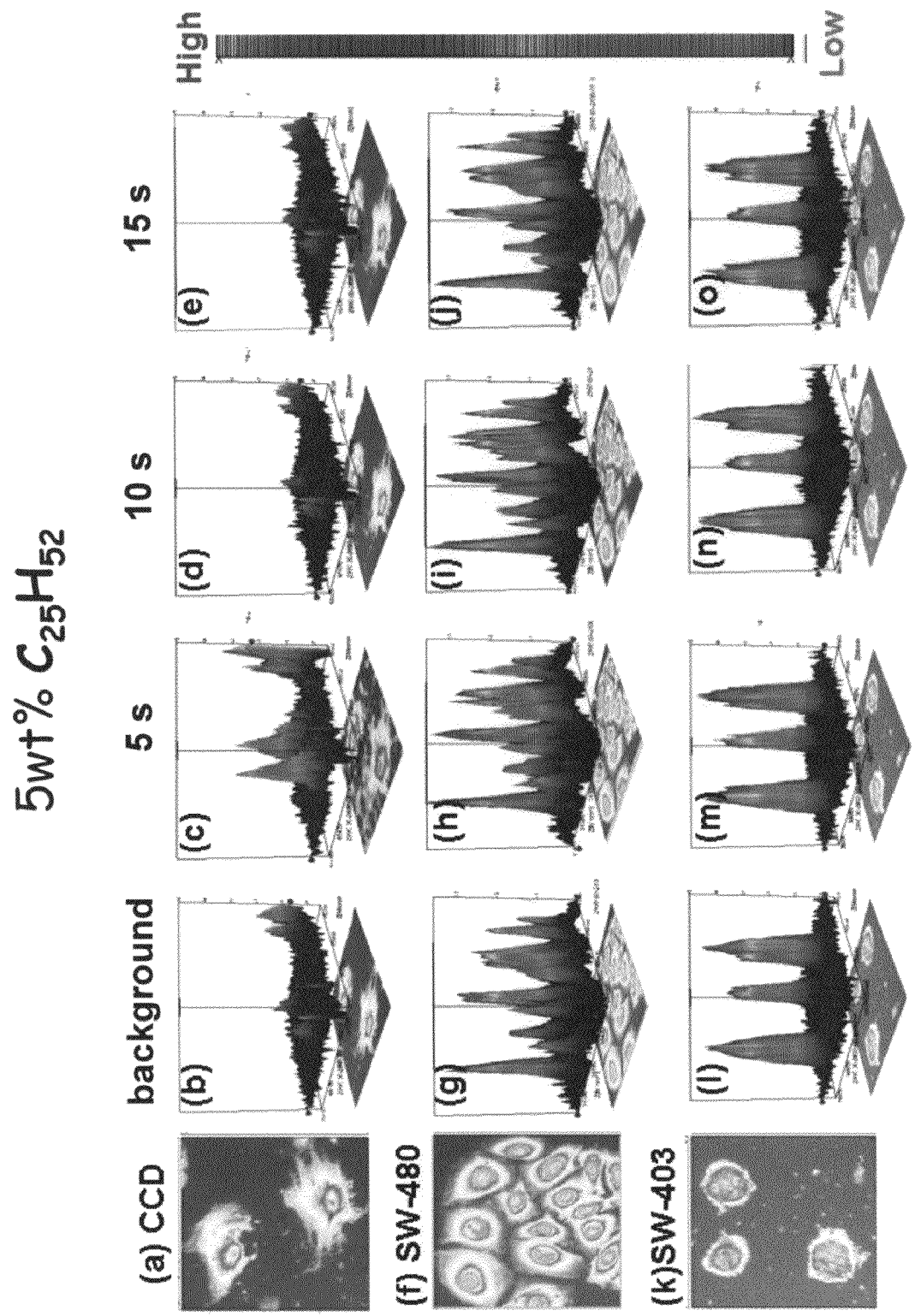
FIG. 3 illustrates infrared spectral images illustrating adsorption of the residue of paraffin adhering onto a cell sample.

FIG. 3 illustrates the infrared spectral images of samples of human cell lines illustrating the results based on the physisorption capability of paraffin. FIG. 3 (a), FIG. 3 (f) and FIG. 3 (k) are visible light images of a sample of normal cell lines CCD-18Co, and two samples of cancer cell lines, SW-480 and SW-403, respectively. FIG. 3 (b), FIG. 3 (g) and FIG. 3 (l) illustrate infrared spectral images of sample cell lines, CCD-18Co, SW-480, and SW-403, respectively, following treatment with xylene for 20 minutes and drying in air. These images serve as reference background images for samples of cell lines after paraffin adsorption and paraffin desorption. FIG. 3 (c-e), FIG. 3 (h-j) and FIG. 3 (m-o) are infrared spectral images of sample of cell lines, CCD-18Co, SW-480 and SW-403, after paraffin desorption for 5 seconds, 10 seconds and 15 seconds, respectively. Comparing reference background images (i.e. the infrared spectral images of cell samples after cleaning with xylene for 20 minutes) with infrared spectral images of cell samples for different time intervals of paraffin desorption; it is observed that the normal cells exhibit an increasing absorbance in the range of 3000-2800 $cm^{-1}$ caused by the paraffin residue onto cell samples. On the contrary, the paraffin adsorbed on cancer cell lines rarely exhibit an increasing absorbance in the range of 3000-2800 $cm^{-1}$ due to less amount of paraffin residues onto the cell samples.

5. A second adsorption step using a second adsorbent, beeswax ($C_{46}H_{92}O_2$), is performed. The infrared absorption spectra of the sample of cell lines is acquired after xylene cleaning of 20 minutes to remove adsorbed paraffin from sample of cell lines and then dry in air. An infrared spectral image of the sample of cell lines is thus constructed based on the spectra of sample of cell lines after xylene cleaning of 20 minutes.

6. A sample of cell lines on a slide is immersed for 2 minutes in a solution of xylene containing 5 wt % beeswax and then taken out of the solution and dried at room temperature.

7. The infrared absorption spectrum and the infrared spectral image of the sample of cell lines are acquired after xylene cleaning of 5 seconds and then air-dried at room temperature, during which the sample of cell lines is beeswaxed and fixed on a slide and desorbed with xylene.

8. The above step 7 is repeated thrice by immersing the sample for 5, 10 and 15 seconds in xylene to desorb completely beeswax.

Figure 4:
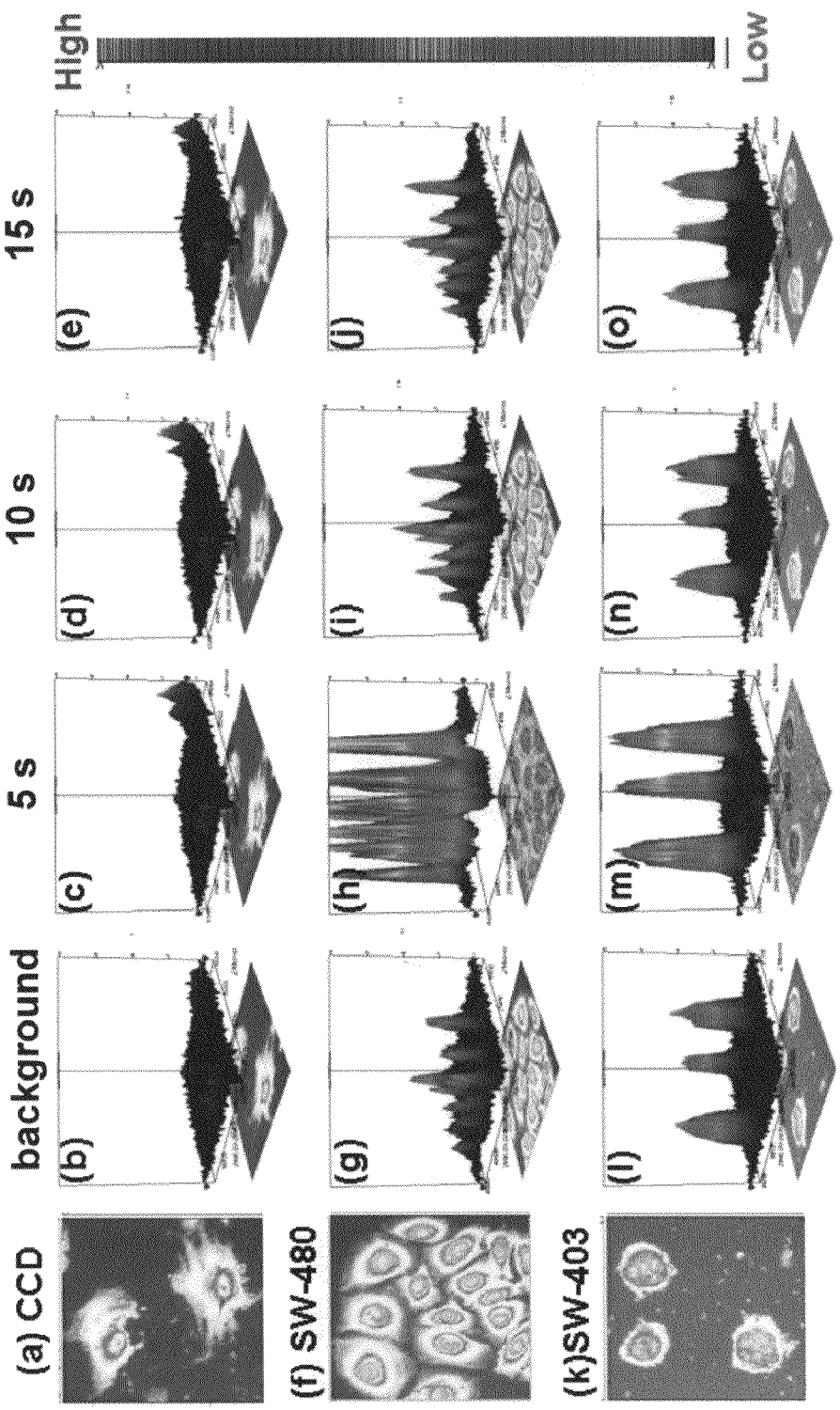
FIG. 4 illustrates infrared spectral images illustrating adsorption of the residue of beeswax adhering onto a cell sample.

FIG. 4 illustrates the result of infrared spectral images illustrating the results of desorption of beeswax from the sample of cell lines.

FIG. 4 (a), FIG. 4 (f) and FIG. 4 (k) are white light images of a sample of normal cell line, CCD-18Co, and two samples of cancer cell lines, SW-480 and SW-403, respectively. FIG. 4 (b), FIG. 4 (g) and FIG. 4 (1) are infrared spectral images of sample of cell lines CCD-18Co, SW-480, and SW-403, respectively, after xylene cleaning of 20 minutes and air-dried, which is constructed based on the absorbance in the range of 3000-2800 $cm^{-1}$. These spectral images serve as reference background images for beeswaxing and debeeswaxing sample of cell lines. FIG. 4 (c-e), FIG. 4 (h-j) and FIG. 4 (m-o) illustrate the infrared spectral images of sample cell lines, CCD-18Co, SW-480 and SW-403 after debeeswaxing by immersing the sample for 5, 10 and 15 seconds. Comparing reference background images (i.e. the infrared spectral images of sample of cell lines after xylene cleaning of 20 minutes) with infrared spectral images of sample of cell lines after xylene cleaning of various time periods, it is observed that the infrared spectral images of cancer cell lines exhibit substantially higher in absorbance within the range of 3000-2800 $cm^{-1}$ due to the beeswax adhered onto the membrane of cancer cell lines. However, the amount of residual of beeswax onto the membrane of normal cell lines is rare. Therefore, the aforementioned method can be rapid and effective in differentiating normal cell lines from cancer cell lines, and can be applied in colorectal cancer detection.

Embodiment 2

Oral Cancer Detection (I)

The aforementioned method may also be adopted in determining oral cavity cancer, wherein there are 5 wt % paraffin and 5 wt % beeswax in xylene using as the first adsorbent and the second adsorbent, respectively.

Figure 5:
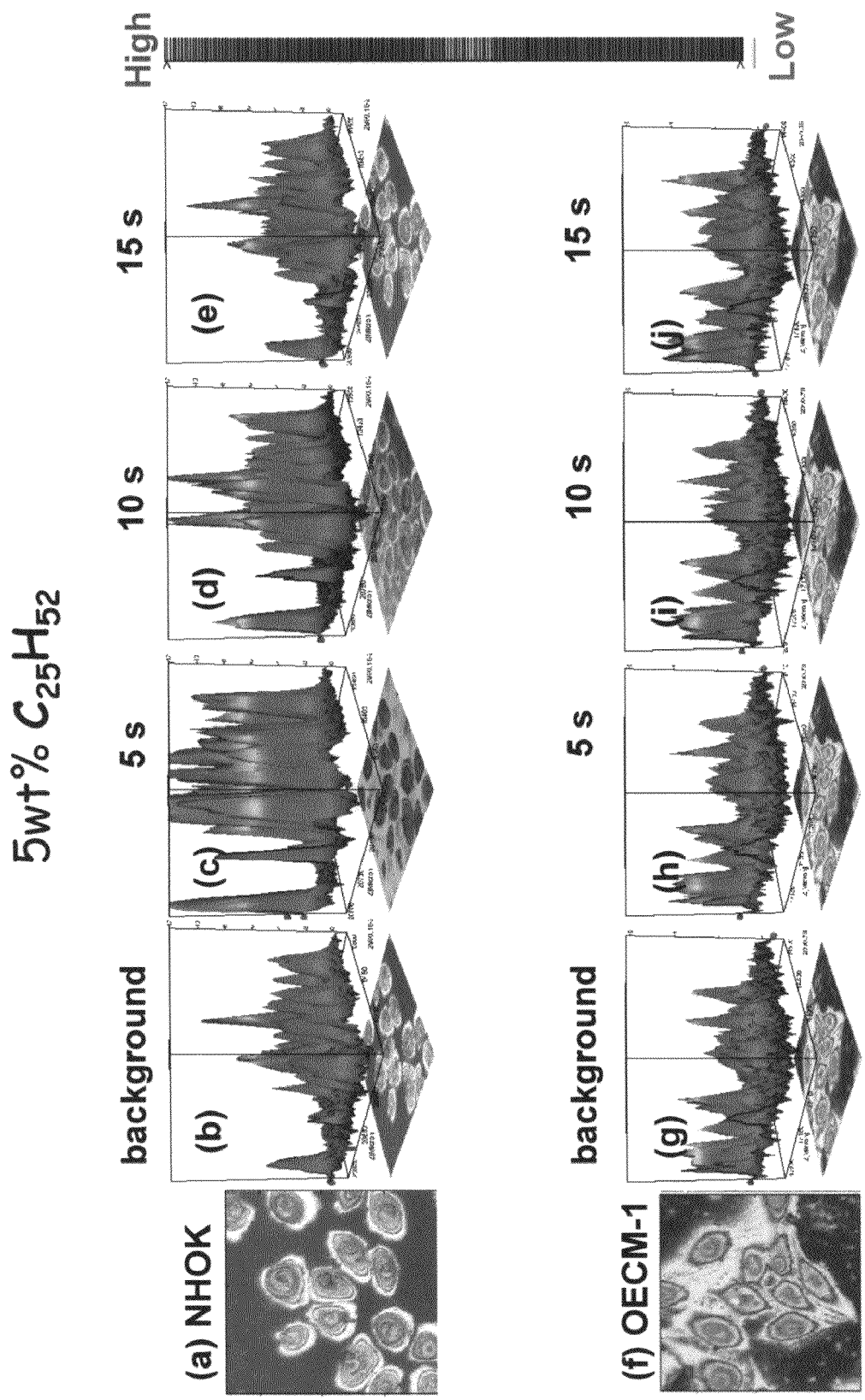
FIG. 5 illustrates infrared spectral images illustrating adsorption of the residue of paraffin adhering onto a cell sample.

FIG. 5 illustrates the result of infrared spectral images illustrating infrared adsorption of paraffined sample cell lines. Both FIG. 5 (a) and FIG. 5 (f) are white light images of samples of normal oral cavity cell lines, normal human keratinocytes (NHOK), and a sample of human oral cavity cancer cell lines, oral epidermoid carcinoma (OECM-1), respectively. FIG. 5(b) and FIG. 5(g) are infrared spectral images of sample cell lines NHOK and OECM-1 after xylene cleaning of 20 minutes and drying at room temperature, which are constructed based on the absorbance in the range of 3000-2800 $cm^{-1}$. These images serve as reference background images for capabilities of paraffin adsorption and desorption. FIG. 5 (c-e) and FIG. 5 (h-j) are infrared spectral images of cell samples NHOK and OECM-1, respectively, after desorption of paraffin for various period of times. Obvious amount of residual of adsorbed paraffin on NHOK compared to that on OECM-1 is illustrated in FIG. 5.

Figure 6:
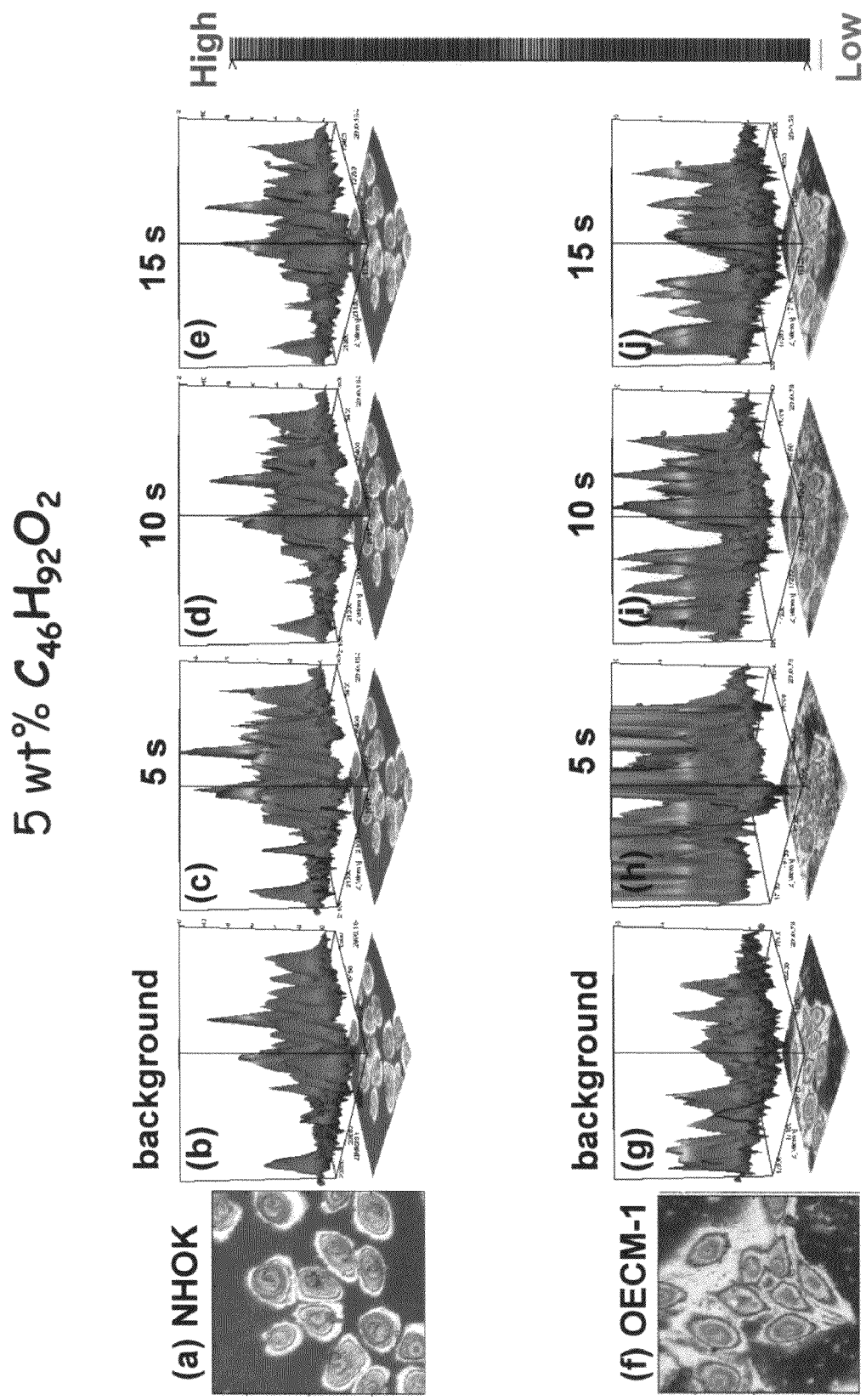
FIG. 6 illustrates infrared spectral images illustrating adsorption of residue of beeswax adhering onto a cell sample.

Additionally, FIG. 6 illustrates the result of infrared spectral images illustrating beeswax adsorption of cell sample. Both FIG. 6(a) and FIG. 6(f) are white light images of samples of normal oral cavity cell lines NHOK and of oral cavity cell lines OECM-1, respectively. FIG. 6(b) and FIG. 6(g) are infrared spectral images of cell lines NHOK and OECM-1 after being cleaned for 20 minutes with xylene and then dried, and the infrared spectral images are constructed based on the absorbance in the range of 3000-2800 $cm^{-1}$. These images serve as reference background images for beeswax adsorption and beeswax desorption; FIG. 6(c-e), FIG. 6(h-j) are infrared spectral images of sample cell lines NHOK and OECM-1, respectively, after desorption of beeswax for various period of times. As can be seen in FIG. 6, the amount of residual of adsorbed beeswax on OECM-1 is substantially more than that on NHOK.

Embodiment 3

Oral Cancer Detection (II)

The procedures for determining the oral cavity cancer according to this method is similar to the process steps 1-8 of embodiment 1 described above, except for the first adsorbent comprises 5 wt % Triacontane ($C_{30}H_{62}$); the second adsorbent comprises 7.5 wt % ethyl myristate ($C_{16}H_{32}O_2$).

Figure 7:
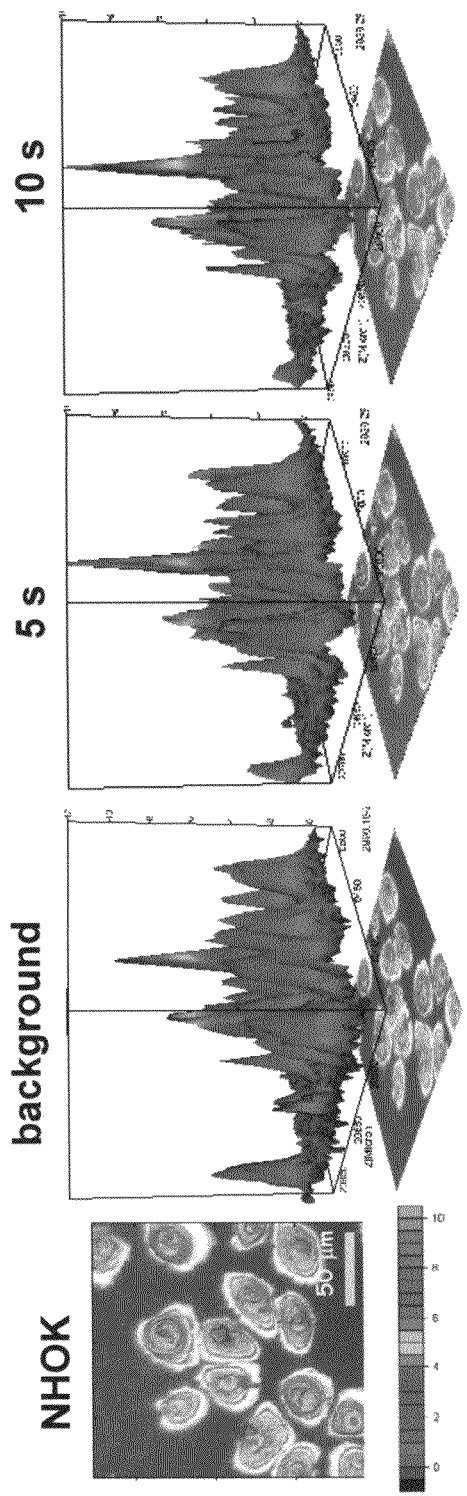
FIG. 7 illustrates infrared spectral images illustrating adsorption of the residue of triacontane ($C_{30}H_{62}$) adhering onto a cell sample.
Figure 7:
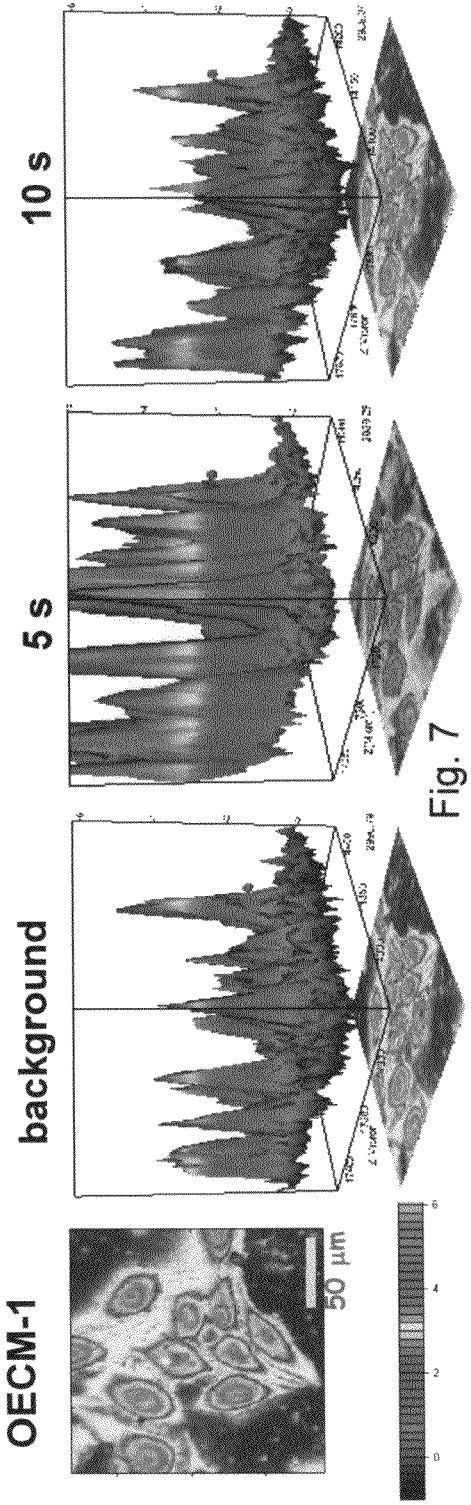

FIG. 7 illustrates the result of infrared spectral images illustrating triacontane ($C_{30}H_{62}$) adsorption onto sample cell lines. Oral squamous cancer cell (OECM-1) lines after adsorption and desorption of triacontane in xylene for 5 seconds also exhibit a characteristic absorption of adsorbed $C_3OH_{62}$ in the spectral range of 3000-2800 $cm^{-1}$.

Figure 8:
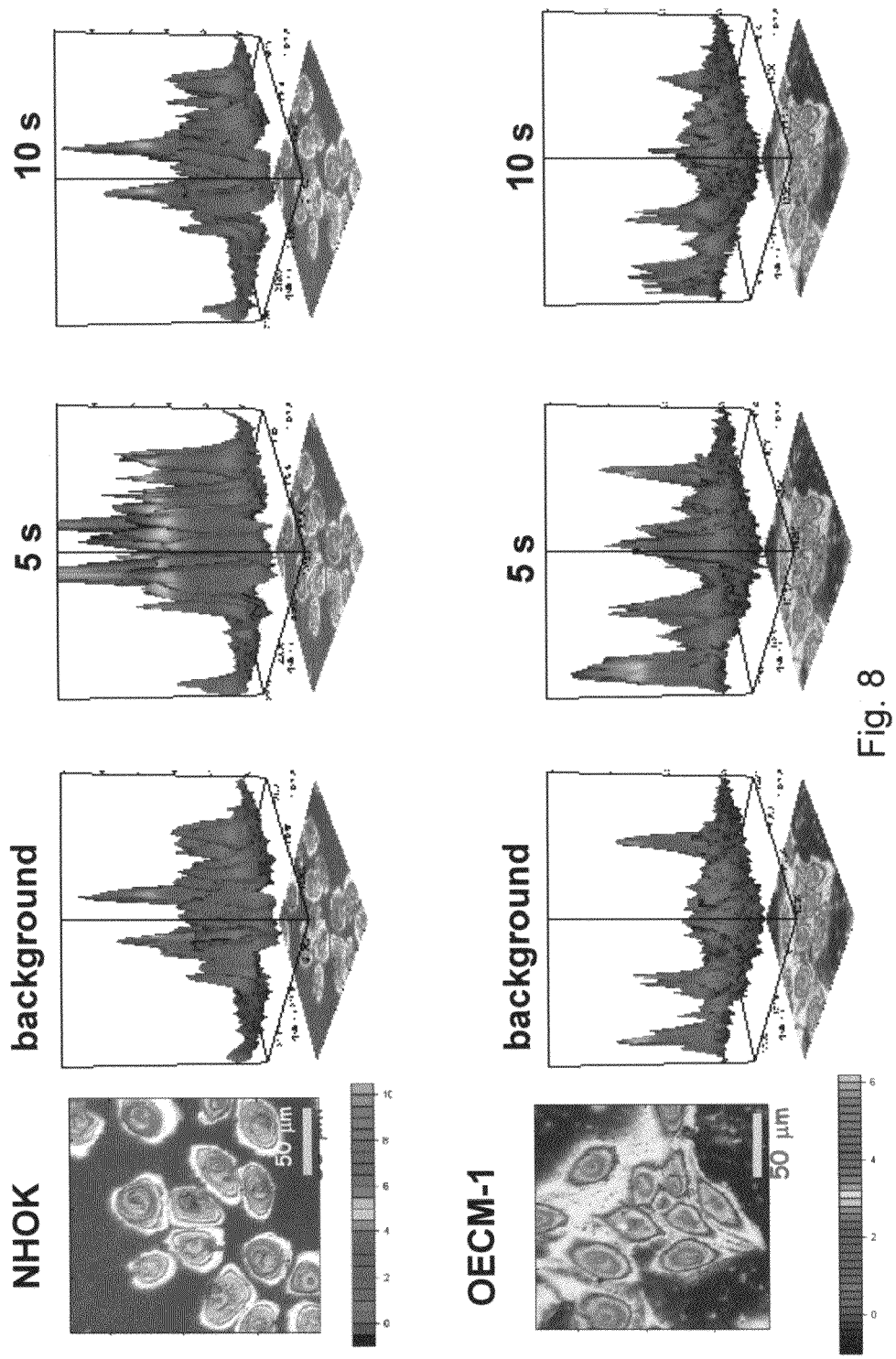
FIG. 8 illustrates infrared spectral images illustrating adsorption of the residue of ethyl myristate ($C_{16}H_{32}O_2$) adhering onto a cell sample.

FIG. 8 illustrates the result of infrared spectral images illustrating ethyl myristate ($C_{16}H_{32}O_2$) adsorption onto sample cell lines. Normal human oral keratinocyte (NHOK) cell lines after adsorption and desorption of ethyl myristate in xylene for 5 seconds exhibit a stronger absorption of adsorbed $C_{16}H_{32}O_2$ in the spectral range 3000-2800 $cm^{-1}$.

Embodiment 4

Detection of Oral Cavity Cancer (III)

The procedure for determining the oral cavity cancer (III) is similar to the process steps 1-4 of embodiment 1 described above, except for the first adsorbent comprises a xylene solution containing 10 wt % 3,5,5-Trimethylhexyl 3,5,5-trimethylcaproat ($C_{18}H_{36}O_2$).

Figure 9:
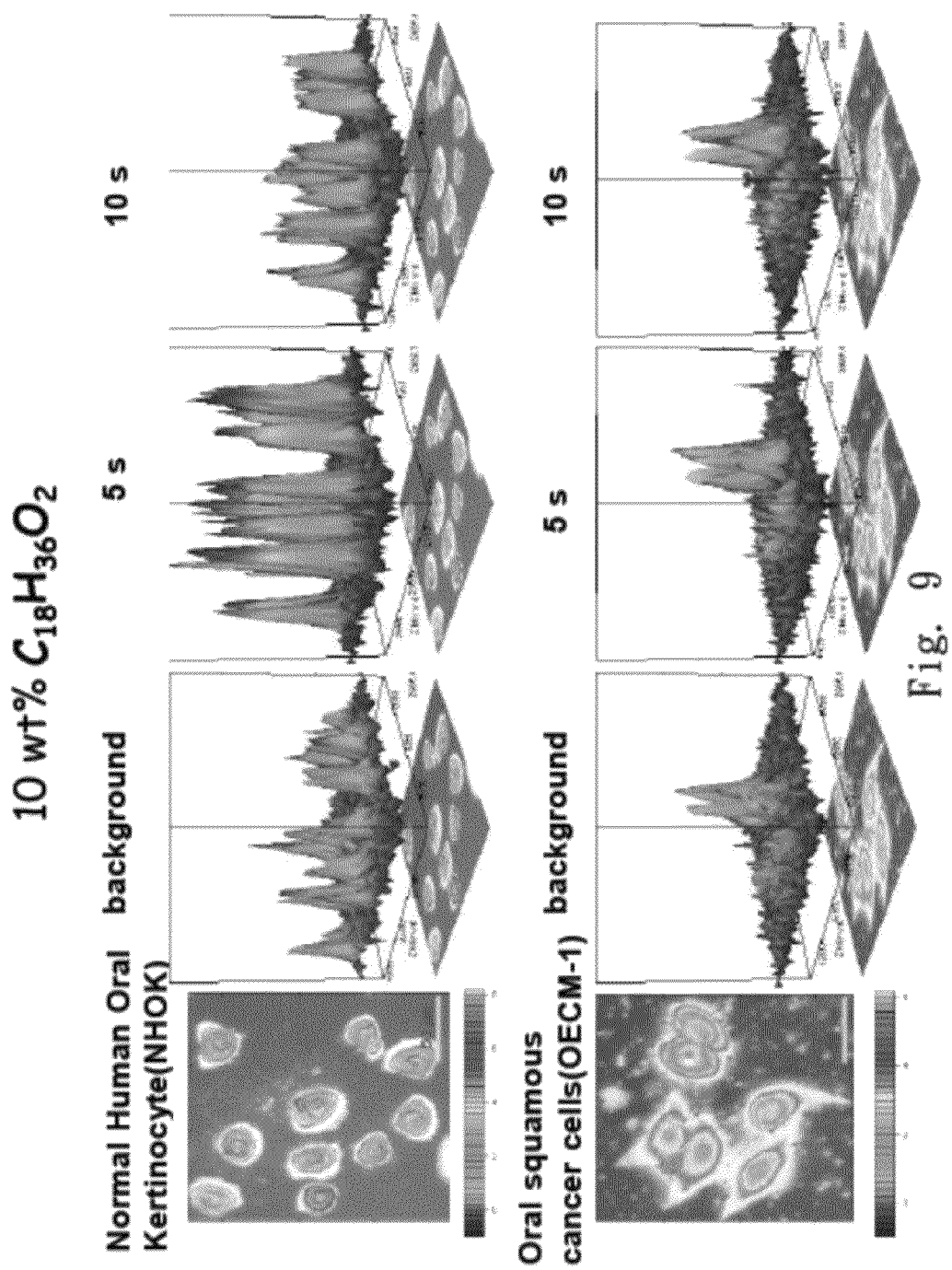
FIG. 9 illustrates infrared spectral images illustrating adsorption of the residue 3,5,5-Trimethylhexyl 3,5,5-trimethylcaproat ($C_{18}H_{36}O_2$) adhering onto a cell sample.

FIG. 9 illustrates the result of infrared spectral images illustrating 3,5,5-Trimethylhexyl 3,5,5-trimethylcaproat ($C_{18}H_{36}O_2$) adsorption onto sample cell lines. Normal human oral keratinocyte (NHOK) cell lines after adsorption and desorption of 3,5,5-Trimethylhexyl 3,5,5-trimethylcaproat in xylene for 5 seconds exhibits a stronger absorption of adsorbed $C_{20}H_{40}O_2$ is in the spectral range 3000-2800 $cm^{-1}$.

Embodiment 5

Detection of Oral Cavity Cancer Tissue

A method for determining the oral cavity cancer tissue may be described as follows.

1. A paraffin-embedded or other material-embedded tissue section sample is fixed on a slide and a suitable solvent is employed to remove embedded material from tissue section sample. After removing the embedded material, and the tissue section sample is cleaned for 60 minutes with xylene to ensure that no residual of embedded material within tissue section before detecting cancer. Finally, infrared spectra of the tissue section sample and the infrared spectral image are obtained to serve as reference background for the following procedures.

2. A tissue section sample is immersed for 10 minutes in a xylene solution containing 5 wt % paraffin as a first adsorbent, and then the tissue section sample is taken out of xylene solution and dried at room temperature.

3. Next, the sample is washed for 30 seconds with xylene and then dried at room temperature, and spectra and spectral images of the tissue section sample are acquired.

4. The above step 3 is repeated twice with 30 and 60 seconds paraffin desorption time periods using xylene solution containing 5 wt % paraffin.

Figure 10:
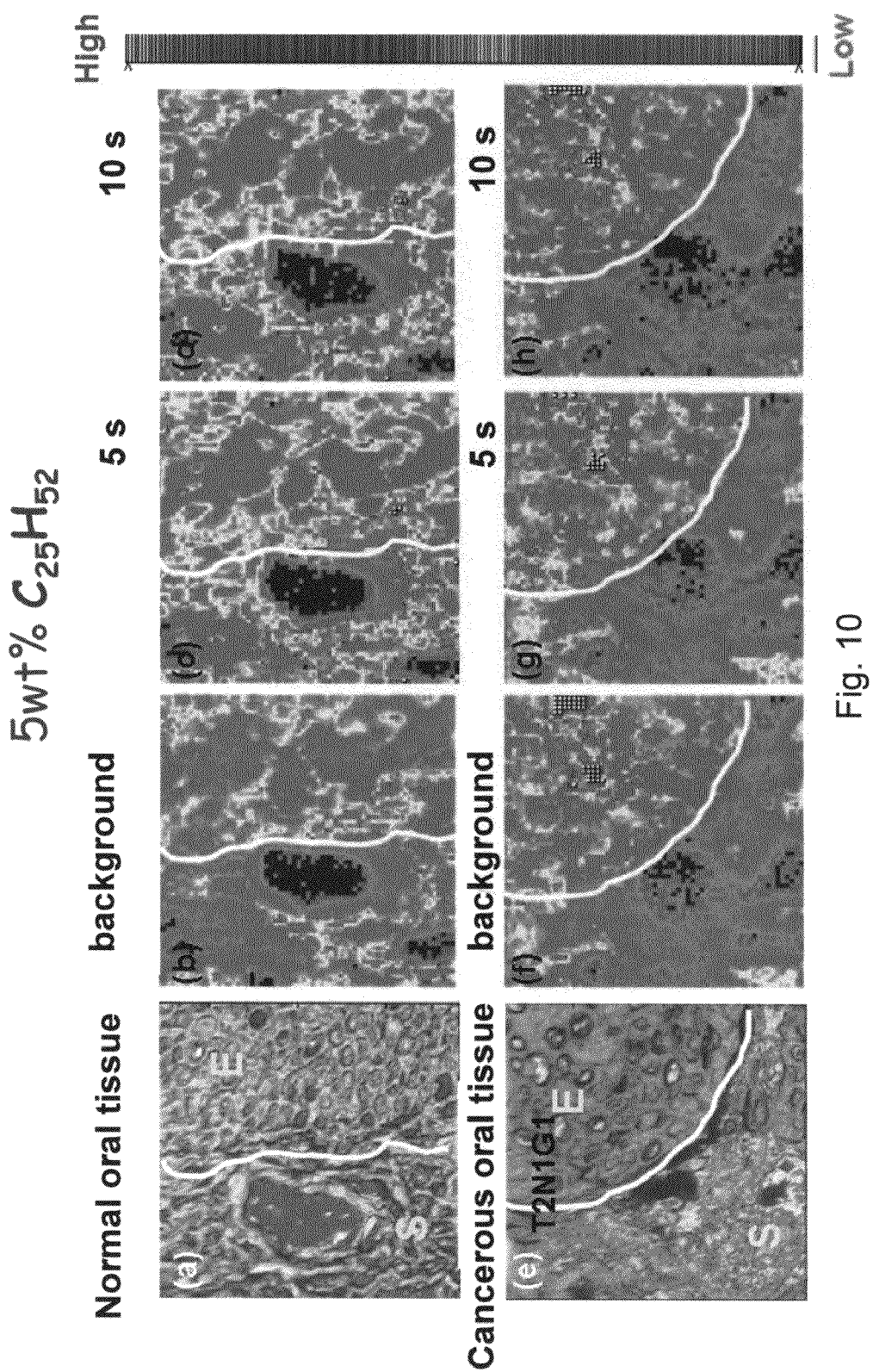
FIG. 10 illustrates infrared spectral images illustrating adsorption of the residue paraffin adhering onto a tissue sample.

FIG. 10 illustrates the result of spectral images illustrating lipid adsorption onto a paraffined tissue section sample. FIG. 10(a) and FIG. 10(e) are white light images of a normal oral cavity tissue section and an oral cavity cancer tissue (T2N1G1) section sample of human, respectively. FIG. 10(b) and FIG. 10(f) are infrared spectral images of a normal oral cavity tissue section and the oral cavity tissue (T2N1G1) section sample after xylene cleaning of 60 minutes and then drying at room temperature, and serve as reference background images for adsorption and desorption of paraffin, which are based on the absorbance within the spectral range of 3000-2800 $cm^{-1}$. FIG. 10(c) and FIG. 10(g) are infrared spectral images of a normal oral cavity tissue section and a oral cavity cancer tissue section sample, respectively, after being cleaned for 30 seconds with xylene to desorb paraffin FIG. 10(d) and FIG. 10(h) are infrared spectral images of a normal oral cavity tissue section and the oral cavity cancer tissue section, respectively, after being treated for 60 seconds with xylene to desorb paraffin.

Comparing the reference background images with the infrared spectral images of oral cavity tissue section samples after desorbing paraffin for variant period of time, the normal tissue section sample illustrates a higher absorbance in the range of 3000-2800 $cm^{-1}$ due to adsorbed paraffin onto the tissue section, on the contrary, the increase of absorbance is not significant in the range of 3000-2800 $cm^{-1}$ due to less adsorbed paraffin on a given oral cavity cancer tissue section sample.

5. A spectrum of a given paraffined oral cavity tissue section sample is acquired after xylene cleaning of 60 minutes and then drying at room temperature.

A spectrum of a given sample of oral cavity tissue section is acquired, which is waxed with second adsorbent, beeswax, after xylene cleaning of 60 minutes for completely removing the beeswax and drying in air at room temperature.

6. A second adsorbent, 5 wt % beeswax in xylene solution, is dripped on a tissue section sample and then dried the tissue section sample in air for 60 minutes at room temperature.

7. An infrared spectrum of a beeswaxed tissue section sample is acquired after xylene cleaning of 30 seconds and drying in air at room temperature.

8. The above step 7 is repeated twice with 30 and 60 seconds debeeswaxing process using xylene solvent.

Figure 11:
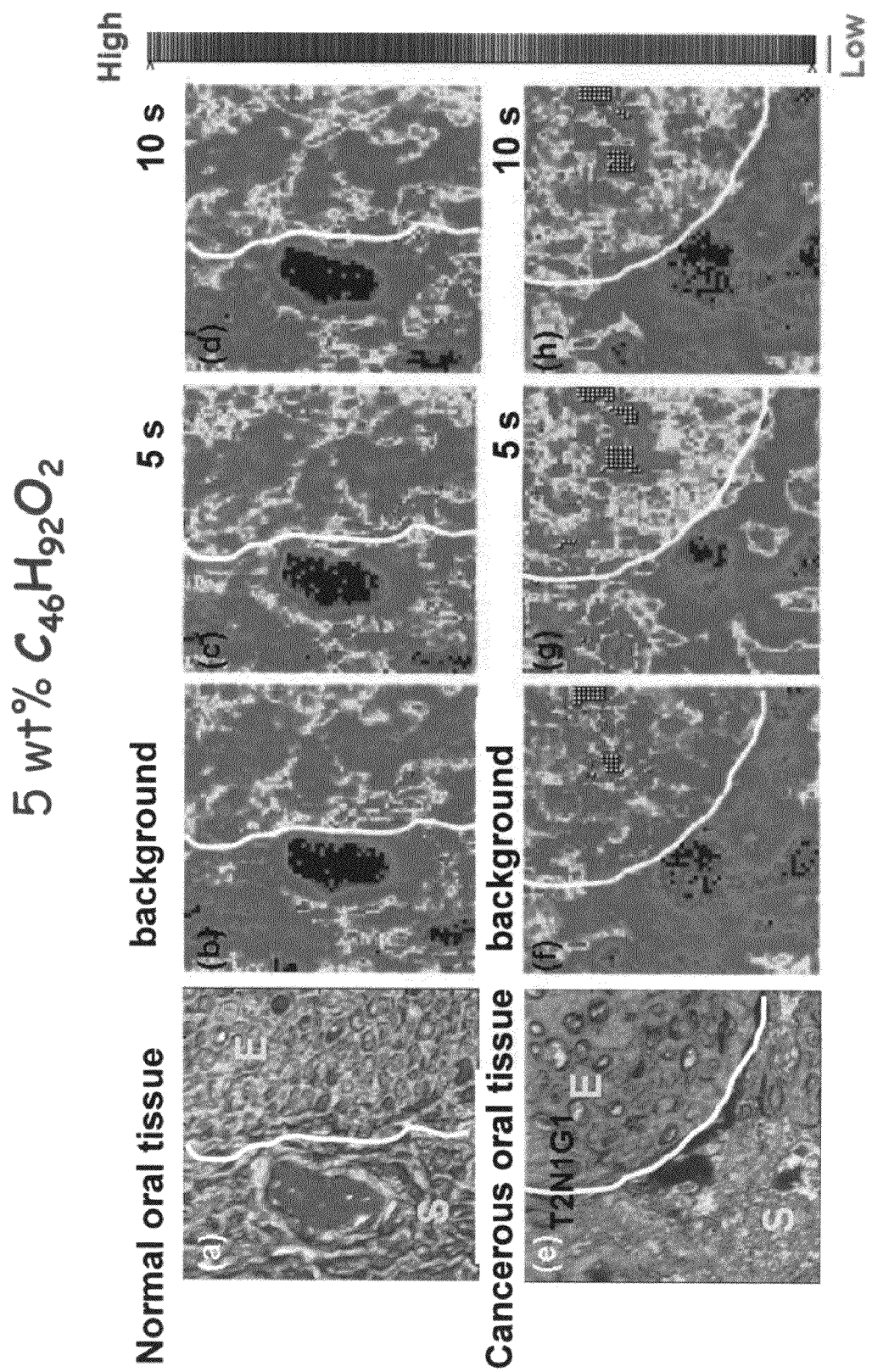
FIG. 11 illustrates infrared spectral images illustrating adsorption of the residue of beeswax adhering onto a tissue sample.

FIG. 11 illustrates the result of spectral images illustrating the residue of beeswax adsorbing onto a tissue section sample. Both FIG. 11(a) and FIG. 11(e) are white light images of a normal oral cavity tissue section and an oral cavity tissue section T2N1G1 of human, respectively. FIG. 11(b) and FIG. 11(f) illustrate the result of infrared spectral images of a normal oral cavity tissue section and an oral cavity cancer tissue (T2N1G1) section in the spectral range of 3000-2800 $cm^{-1}$ after xylene cleaning of 20 minutes and drying in air at room temperature. These images serve as reference background images for beeswaxing and debeeswaxing of tissue section sample. FIG. 11(c) and FIG. 11(g) are infrared spectral images of a normal oral cavity tissue and an oral cavity cancer tissue section, respectively, after xylene cleaning of 30 seconds to desorb beeswax. FIG. 10(d) and FIG. 10(h) are infrared spectral images of a normal oral cavity tissue section and an oral cavity cancer tissue section, respectively, after xylene cleaning of 60 seconds.

Comparing the reference background images with the infrared spectral images of oral cavity tissue sections after debeeswaxing for various period of time intervals, it is observed that the oral cavity cancer tissue section exhibits an increase of absorbance in the spectral range 3000-2800 $cm^{-1}$ caused by more residue of beeswax. On the contrary, the absorbance of beeswax adsorbed onto the normal oral cavity tissue section is low. Therefore, the said method can be applied to rapidly and effectively differentiate malignant part from a biomedical tissue, and can be applied to detect oral cavity cancer and colon cancer.

Embodiment 6

Cancer Diagnosis Utilizing Florescence Microscopy

1. First, a sample of cell lines is fixed on a slide and then cleaned for 20 minutes with xylene, and measured by an optical microscope.
2. A reagent of dye-beeswax-xylene solution containing 0.01 wt % dye and 5 wt % beeswax is used for differentiating cancer cell lines from normal cell lines. The sample is immersed in dye-beeswax-xylene solution for 1 minute and then dried in air at room temperature.
3. Fluorescence images of a sample of cancer cell lines are acquired after xylene cleaning of 5 seconds in and drying in air.
4. The above step 3 is repeated twice with 5 and 10 seconds of debeeswaxing process with xylene solvent.

Figure 12:
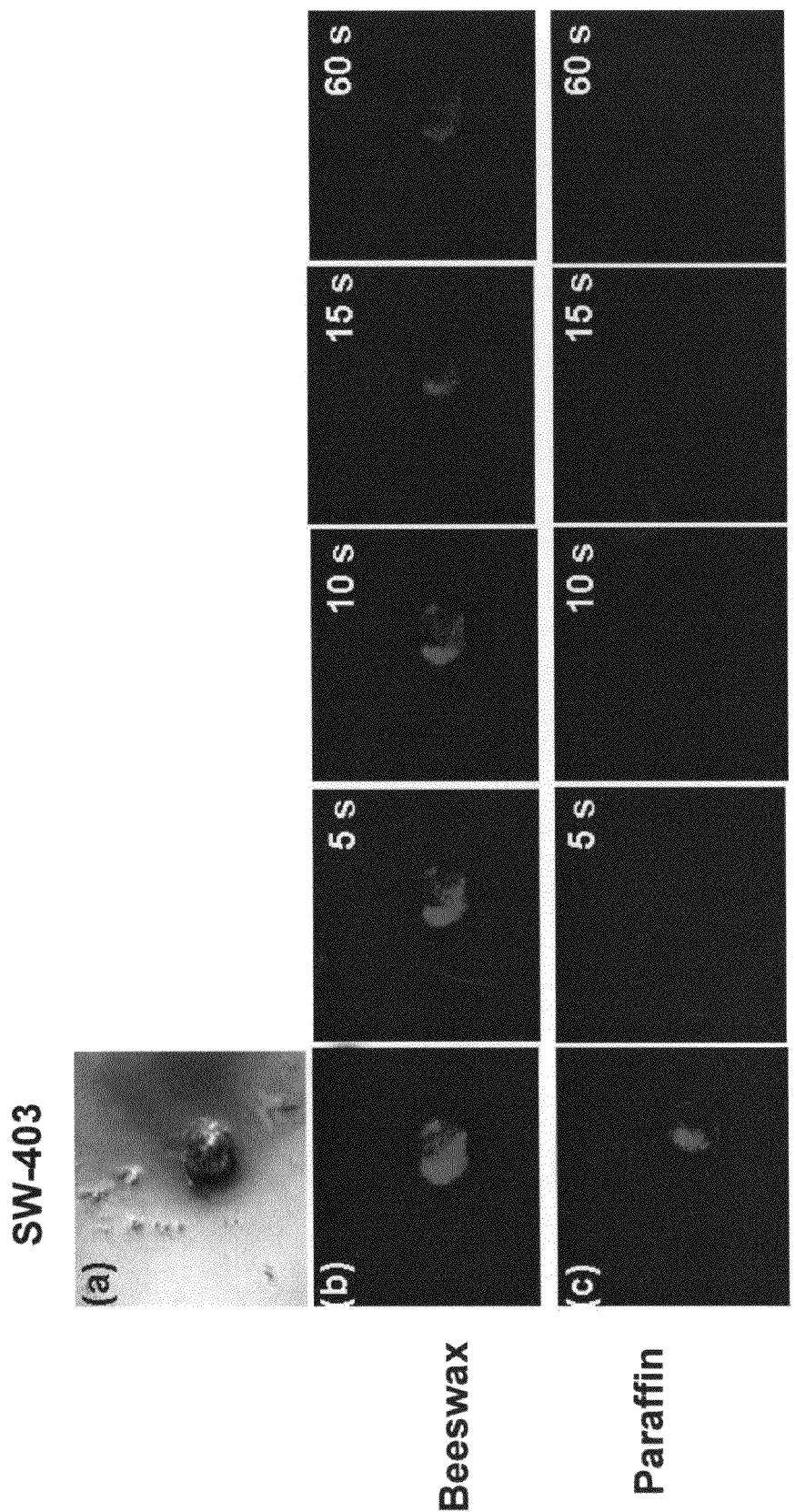
FIG. 12 illustrates fluorescence images illustrating adsorption of the residue of dye-wax reagent adhering onto a tissue sample.

FIG. 12 illustrates the results of fluorescence images illustrating beeswax adsorption onto the sample of cell lines. FIG. 12(a) is a white light image of cancer cell lines of SW-403. FIG. 12(b) illustrates a control image without debeeswaxing and those images of debeeswaxed cancer cell lines of SW-403 after being debeeswaxed for a duration of 5, 10, 15 and 60 seconds, respectively. FIG. 12(c) illustrates an image without being deparaffined and those images of cancer cell lines of SW-403 after deparaffining for a duration of 5, 10, 15 and 60 seconds, respectively. The result showed that more intense fluorescence is exhibited by the residual beeswax adsorbed onto the sample of cancer cell lines In summary, a method for cancer detection of the present invention is based on the physisorption capability of detection reagent onto samples of cancer cell lines and normal cell lines. The method employing the said principle can be a rapid and non-invasive method, and sample can also be re-examined for further medical inspection.

While the invention is susceptible to various modifications and alternative forms, a specific example thereof has been shown in the drawings and is herein described in detail. It should be understood, however, that the invention is not to be limited to the particular form disclosed, on the contrary, the invention is to cover all modifications, equivalents, and alternatives falling within the spirit and scope of the appended claims.

What is claimed is:

1. A method for detecting cancer, comprising:
providing a biomedical sample suspected of being cancerous;
performing a first adsorption step comprising immersing the biomedical sample into a first detection reagent comprising a first adsorbent that adsorbs onto the biomedical sample, wherein a concentration of the first adsorbent is between 5% to 10% w/w and the first adsorbent comprises a long-chain ester containing 16-46 carbon atoms or a long-chain alkane containing 21-30 carbon atoms;
performing a first desorption step comprising immersing the biomedical sample into a first desorption reagent for a first period of time;
performing a first discrimination step comprising measuring an amount of residual of first adsorbent adsorbed onto the biomedical sample in comparison to an amount of residual of first adsorbent adsorbed onto a normal biomedical sample or a cancerous biomedical sample to determine if cancer cells are distributed within the biomedical sample being tested;
performing a second adsorption step comprising immersing the biomedical sample into a second detection reagent comprising a second adsorbent that adsorbs onto the biomedical sample;
performing a second desorption step comprising immersing the biomedical sample into a second desorption reagent for a second period of time; and
performing a second discrimination step comprising measuring an amount of residual of second adsorbent adsorbed onto the biomedical sample to determine if the cancer cells are distributed within the biomedical sample being tested;
wherein the second adsorbent comprises a long-chain alkane containing 21-30 carbon atoms.

2. The method as claimed in claim 1, wherein the first desorption step and the first discrimination step are repeated for at least one time.

3. The method as claimed in claim 1 further comprising a step of performing a first pre-cleaning step before the first adsorbing step comprising immersing the biomedical sample into the first desorption reagent for a longer period of time than the first period of time.

4. The method as claimed in claim 1, wherein the first desorption reagent comprises an organic solvent.

5. The method as claimed in claim 1, wherein the second desorption step and the second discrimination step are repeated for at least one time.

6. The method as claimed in claim 1, wherein a physisorption capability of the first adsorbent for the cancer cells is greater than that of normal cells in the biomedical sample, and a physisorption capability of the second adsorbent for the normal cells is greater than that of the cancer cells in the biomedical sample.

7. The method as claimed in claim 1 further comprising:
performing a second pre-cleaning step prior to the second adsorption step comprising immersing the biomedical sample into the second desorption reagent for a third predetermined period of time which is longer than the second predetermined period of time.

8. The method as claimed in claim 1, wherein the first desorption reagent and the second desorption reagent comprise an organic solvent.

9. The method as claimed in claim 1, wherein the first detection reagent further comprises a dye having greater physisorption capability for the first adsorbent than that for the biomedical sample.

10. The method as claimed in claim 9, wherein the dye is a fluorescent dye.

11. The method as claimed in claim 10, wherein a relative amount of residual of the first adsorbent adsorbed is detected by measuring fluorescence images.

12. The method as claimed in claim 10, wherein the fluorescent dye comprises LC6500, 4-dicyanomethylene-2-methyl-6-p-dimethylaminostyryl-4H-pyran (DCM), Allophycocyanin (APC) or APC-Cy7.

13. The method as claimed in claim 1, wherein a relative amount of residual of the first adsorbent adsorbed is detected by measuring an infrared spectrum or a Raman scattering spectrum.

14. The method as claimed in claim 13, wherein the spectral range of the infrared spectrum is within 3000-2800 $cm^{-1}$.

15. The method as claimed in claim 13, wherein the Raman shift of the Raman scattering spectrum is within 3000-2800 $cm^{-1}$.

16. The method as claimed in claim 1, wherein the biomedical sample comprises a tissue section or cell lines.

17. The method as claimed in claim 1, wherein the cancer tissue section comprises an oral cavity cancer tissue section or a colon cancer tissue section.

18. A method for detecting cancer, comprising:
   providing a biomedical sample suspected of being cancerous;
   performing a first adsorption step comprising immersing the biomedical sample into a first detection reagent comprising a first adsorbent that adsorbs onto the biomedical sample;
   performing a first desorption step comprising immersing the biomedical sample into a first desorption reagent for a first period of time;
   performing a first discrimination step comprising measuring an amount of residual of first adsorbent adsorbed onto the biomedical sample in comparison to an amount of residual of first adsorbent adsorbed onto a normal biomedical sample or a cancerous biomedical sample to determine if cancer cells are distributed within the biomedical sample being tested;
   performing a second adsorption step comprising immersing the biomedical sample into a second detection reagent comprising a second adsorbent that adsorbs onto the biomedical sample;
   performing a second desorption step comprising immersing the biomedical sample into a second desorption reagent for a second period of time; and
   performing a second discrimination step comprising measuring an amount of residual of second adsorbent adsorbed onto the biomedical sample to determine if the cancer cells are distributed within the biomedical sample being tested;
   wherein the first adsorbent comprises a long-chain alkane containing 21-30 carbon atoms and the second adsorbent comprises a long-chain ester containing 16-46 carbon atoms.

* * * * *